United States Patent [19]
de Vos, Sr. et al.

[11] Patent Number: 5,415,054
[45] Date of Patent: May 16, 1995

[54] MULTI COLOR PRINTABILITY TESTING APPARATUS

[75] Inventors: Ferdinand A. de Vos, Sr., Cherry Hill, N.J.; Leon A. de Vos, Zaandam, Netherlands; Aaron L. Black, Cherry Hill, N.J.

[73] Assignee: Research North America, Inc., Cherry Hill, N.J.

[21] Appl. No.: 951,214

[22] Filed: Sep. 25, 1992

[51] Int. Cl.6 .................. G01N 33/00; G01L 5/04
[52] U.S. Cl. .................................... 73/866; 73/159
[58] Field of Search .............. 73/866, 159; 364/471; 356/429, 430, 431; 250/571, 572

[56] References Cited

U.S. PATENT DOCUMENTS

| | | |
|---|---|---|
| 4,041,770 | 8/1977 | Staheli ........................ 73/159 |
| 4,676,094 | 6/1987 | Hoffman et al. .............. 73/159 |
| 4,803,872 | 2/1989 | Crawford et al. ............. 73/159 |
| 4,898,037 | 2/1990 | Allen et al. .................. 73/866 |

OTHER PUBLICATIONS

IGT-Printability Tester-A1C 2-5, Exploded Assembly Drawing, 1980 (2 sheets).
Instruction Manual IGT Printability Tester A1C2-5, Serie V, 1989 (34 pages).
Reprotest B.V., Equipment for Material, Product and Process Testing in the Printing and Allied Industries, 10th Ed., 1990 (48 pages).
Reprotest B.V Literature (4 pages) undated.

*Primary Examiner*—Richard E. Chilcot, Jr.
*Assistant Examiner*—William L. Oen
*Attorney, Agent, or Firm*—Volpe and Koenig

[57] ABSTRACT

An improved testing apparatus for examining printing materials. The testing apparatus is comprised of a rotatable sector that is rotated at selected, controlled speeds. At least one rotatable printing disk, mounted adjacent to the sector, is moved by fluid drive means into and out of contact with a test strip mounted on the sector. The pressure with which the disk is applied to the sector is continuously monitored and held constant to maintain the printing pressure at the desired level. A programmable controller controls the speed and position of the sector and the movement and contact pressure of the disk relative to the sector.

20 Claims, 5 Drawing Sheets

MULTI COLOR PRINTABILITY TESTING APPARATUS

BACKGROUND OF THE INVENTION

1. Field of the Invention

The present invention relates to equipment for material, product, and process testing. More particularly, the present invention finds use in the testing of various printing inks, coatings, pulps, papers and chemicals of the type used by the printing industry. Most particularly, the present invention provides a portable tester for accurately and reliably testing the effects of varying factors such as printing pressures, printing speeds, delay intervals and printing materials.

2. Description of the Prior Art

The need to examine the properties of incoming printing materials has been generally recognized in the printing industry. The high production speeds and large printing formats of modern printing presses make down-time for testing and adjustments an expensive matter. The effective examination and testing of printing materials can provide the data required to set and adjust the printing presses for variations in the materials. Therefore, the need for an accurate and reliable means for testing printing materials prior to their use is desired in order to avoid the loss of production and to maintain the quality of the printed materials has been recognized.

In order to fill the need for testing printing materials, printability testers have been developed. These testers are used to examine printing materials with respect to such variables as ink film thickness, printing pressure, printing speeds and delay intervals which are present during any printing process. Various standardized tests such as dry pick, wet pick, wet repellency, flexographic, gravure, set off, one-color and two-color printing have been used to determine what these variables should be with respect to the various materials in order to achieve the desired results. The printing industry recognizes ISO standards that have been developed and promulgated for some of these tests.

The printability testers in use today still utilize mechanical systems which cannot always meet the requirements for testing modern materials. These testers provide a sector, or common impression cylinder, upon which a test strip of printing paper is mounted. One of two printing disks, coated with a predetermined amount of ink or other print testing material, are applied at a given pressure to the test strip mounted on the sector. The sector is then rotated at a given speed causing the printing disk or disks to print on the test strip. The sector can be rotated at a constant uninterrupted speed, or it can be stopped halfway through its rotation and then continue after a preset time interval. After the sector has rotated a predetermined distance, generally equal to the length of a test strip, a mechanical cam lifts the printing disks off of the sector. The test strip is then removed and examined to determine the effects of various parameters such as speed, printing pressure, and drying time on the materials.

The printing pressure is applied to the disks during testing using hand-adjustable springs which may impart a force of up to 1000 newtons. The disks are manually brought into contact with the sector before the sector drive system is engaged. After the sector rotates a predetermined distance which is less than a full circle, but generally the length of the test strip, a cam lifts the disk or disks from the sector. The cam and drive mechanisms must therefore have sufficient energy to overcome the printing disk spring force.

These prior art testing machines typically weigh more than 250 pounds and are generally powered by large three-phase 380 volt or 440 volt motors. The basic systems are mechanical and require a large flywheel to store the energy required to operate the mechanical systems. In use, the heavy loads cause the tester to vibrate; this results in variations of pressure with which the printing discs are applied during testing.

The existing printability testers are also not user-friendly. In order to mount a test strip on the sector, the operator has to manually turn the sector while it is still loaded by the mechanical system and linkages in the tester. The operator also has to be trained in printability testing and needs to manually set the tester for each different type of test to be performed. All test data must also be manually read from the settings on the machine and recorded by the operator.

SUMMARY OF THE INVENTION

The present invention provides an improved testing apparatus for examining printing materials. The testing apparatus is comprised of rotatable sector that is rotated by a drive means at selected, controlled speeds. The sector's rotary position is continuously monitored. At least one rotatable printing disk is mounted adjacent to the sector for movement into and out of contact of the sector. Fluid drive means are used to move the rotatable printing disk into and out of contact with the sector. The pressure with which the disk is applied to the sector is continuously monitored and held constant to maintain the printing pressure at the desired level. A programmable controller communicates with the sector drive means and controls the speed and position of the sector and the movement and contact pressure of the disk relative to the sector.

It is an object of this invention to provide a portable testing apparatus for examining printing materials.

It is an object of this invention to provide a testing apparatus for examining printing materials in which the disks can be independently engaged and disengaged from the sector.

It is an object of this invention to provide a testing apparatus for examining printing materials in which the sector is capable of full circle rotation and multiple turns.

It is an object of this invention to provide a testing apparatus for examining printing materials in which two, three or four printing disks, each capable of independent movement into and out of contact with the sector, can be applied at varying intervals to a test strip.

It is an object of this invention to provide a printing materials testing apparatus which utilizes a menu driven computer controller and can be easily programmed by an operator following the menus to input the data required for performing various tests.

It is an object of this invention to provide a printing materials testing apparatus which is capable of downloading test data for printing labels and/or for storage on computers or other electronic media.

DESCRIPTION OF THE PREFERRED EMBODIMENTS

Figure 1:
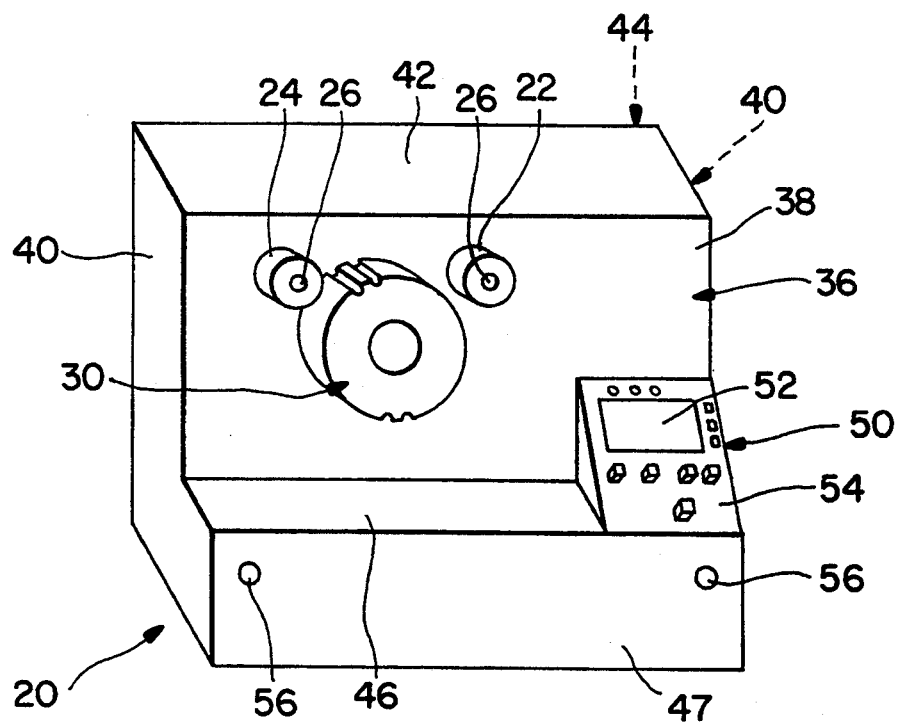
FIG. 1 is a perspective view of a preferred embodiment of the invention.

Referring to FIGS. 1 through 4, there is shown a first embodiment of the testing apparatus 20 according to the present invention. As shown in FIG. 1, sector or common impression cylinder 30 is rotatably mounted in front of the front panel 38 of the housing 36. The sector 30 contains slots 31 for retaining the ends of a strip of test paper. The two printing disks 22 and 24 are rotatably mounted adjacent to the sector 30 for movement into and out of contact with the sector 30. The housing 36 is comprised of the front panel 38, two sides 40, a top 42 and a back 44. An apron 46 and a lower access panel 47 extend forward from below the front panel. Located on the apron 46 of the housing 36 is a control panel 54 for a computer controller 50. A display 52 provides the operator with menu-driven prompts for programming the controller 50 to select and run the various printability tests. Two separated start buttons 56 are provided on either side of the access panel 47 for safety reasons.

Figure 2:
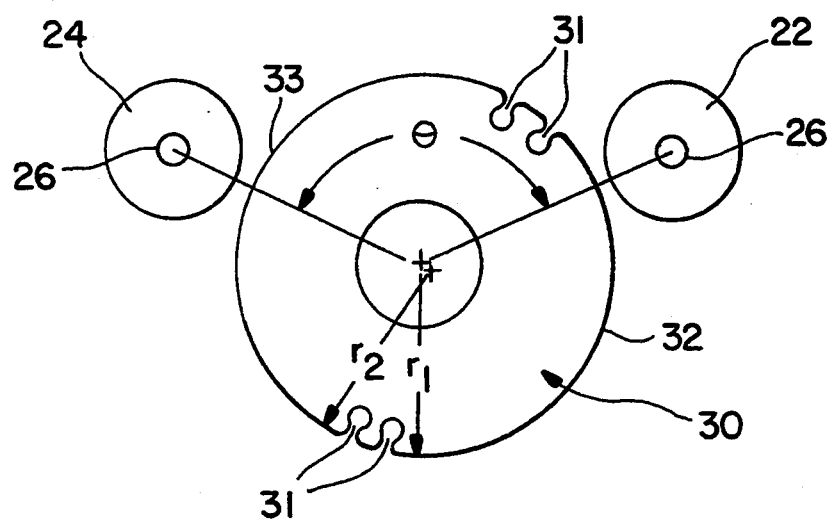
FIG. 2 is an enlarged view of a portion of the front of the testing apparatus embodying this invention.

Referring to FIG. 2, the geometries of the sector 30 and disks 22 and 24 and their special relationship are shown. The sector 30 is generally circular in form, but is modified from a true circle. The impression portion 32 of sector 30 upon which a test strip of paper is to be mounted has a radius $r_1$. The slots 31 for mounting a test strip bound either side of the impression portion 32. The radius $r_1$ for the impression portion 32 of the sector 30 is centered along the axis of rotation of the sector. The remaining portion of the periphery of the sector 30 has a relief 33. Relief 33 is accomplished by machining that portion of the sector with a radius of $r_2$ which is offset from the axis of rotation of the sector 30. Thus the offset portion 33 has a shorter effective radius with respect to the axis of rotation of the sector 30 than $r_1$. This condition is illustrated in FIG. 2. In operation, only the impression portion 32 of the sector 30 is contacted by the disks 22 or 24.

The disks 22 and 24 are located adjacent to sector 30 and are spaced apart by $\Theta°$. $\Theta$ is defined as the angle formed by lines extending through the center of the sector 30 and the respective center of each of the disks 22 and 24. In the preferred embodiment, $\Theta$ is approximately 135° or greater and the direction of rotation of the sector 30 is counter-clockwise. The disks 22 and 24 are approximately 65 mm in diameter and the sector 30 has a radius of approximately 85 mm. By using the 135° spacing in conjunction with an 85 mm radius for the sector 30, a standard 20 cm long test strip can be fully coated by the first disk 22 before reaching the second disk 24.

The printing disks can be made from a variety of materials and may also have a rubber or polyurathane coating on the printing surface. Each disk 22 and 24 contains an aperture 26 for mounting the disks. In operation, the disks are independently moved into and out of contact with the sector 30 and are driven by contact with the sector. By utilizing a spacing angle of 135° or greater and independently movable disks, it is possible to make complete single or a variety of double prints of an entire test strip.

Figure 3:
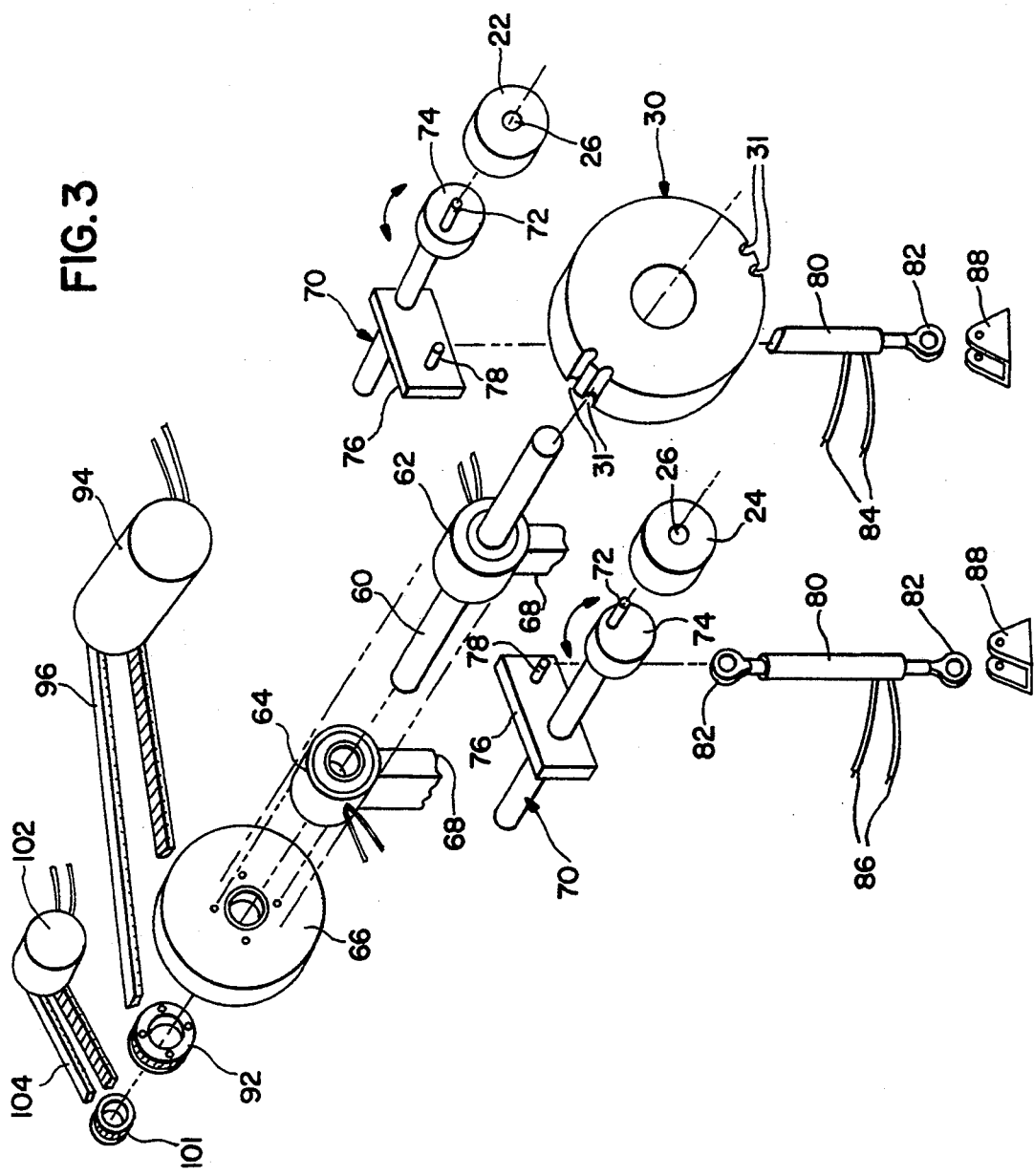
FIG. 3 is an exploded perspective view of the drive systems for the sector and the printing discs of FIG. 1. The testing apparatus housing has been omitted for clarity.

FIG. 3 shows the drive systems utilized for rotating the sector 30 and moving the disks 22 and 24 into and out of contact with the sector 30. The housing 36 has been omitted for clarity. The sector 30 is mounted on the front end of the sector drive shaft 60. An electric brake 62, an electro-magnetic clutch 64 and a flywheel 66 are disposed on the drive shaft 60. The drive shaft 60 and sector 30 are freely rotatable with respect to the brake 62, clutch 64 and flywheel 66 when the testing apparatus 20 is not in the test mode. A permanent magnet D.C. motor 94, using standard 110 or 220-volt single phase power, and a belt 96 are used to drive a pulley 92 attached to the flywheel 66. When energized, the clutch 64 engages the flywheel 66 to the drive shaft 60 to turn both the drive shaft 60 and the sector 30. When the clutch 64 is disengaged, the brake 62 is activated to stop the drive shaft 60.

A rotary encoder 102 is used to generate data on the position of the sector drive shaft 60 and the sector 30. A second pulley 101, attached to the back end of the sector drive shaft 60, and a toothed belt 104 are used to turn rotary encoder 102. The sector's rotary position is continually signaled to the computer controller 50 by the rotary encoder 102.

The disks 22 and 24 are each moved independently into and out of contact with the sector 30 by a respective pneumatic actuator 80 acting on a respective disk positioning shaft 70. Each disk 22 or 24 is rotatably disposed on a respective spindle 72 affixed to the front end 74 of each disk positioning shaft 70. The axis of each spindle 72 is offset from the axis of rotation of its respective disk positioning shaft 70. A lever arm 76 with an actuator attachment shaft 78 is attached to each disk positioning shaft 70. The actuators 80 have rod ends 82, with spherical bearings, affixed to each end thereof. The upper rod ends 82 are disposed on the respective actuator attachment shafts 78. The opposite rod ends 82 are pinned to clevis attachments 88 at a fixed point inside the housing 36. The actuator 80 controls the position of shaft 70. With this arrangement, the offset positioning of spindle 72 causes the translation of each disk 22 or 24 into and out of contact with the impression area 32 on the sector 30. The disk apertures 26 are sized for a running fit with the spindles 72.

Both the sector drive shaft 60 and the disk positioning shafts 70 are supported for rotary movement by bearings (not shown) mounted in the front panel 38 and back 44 of the housing 36.

Figure 4:
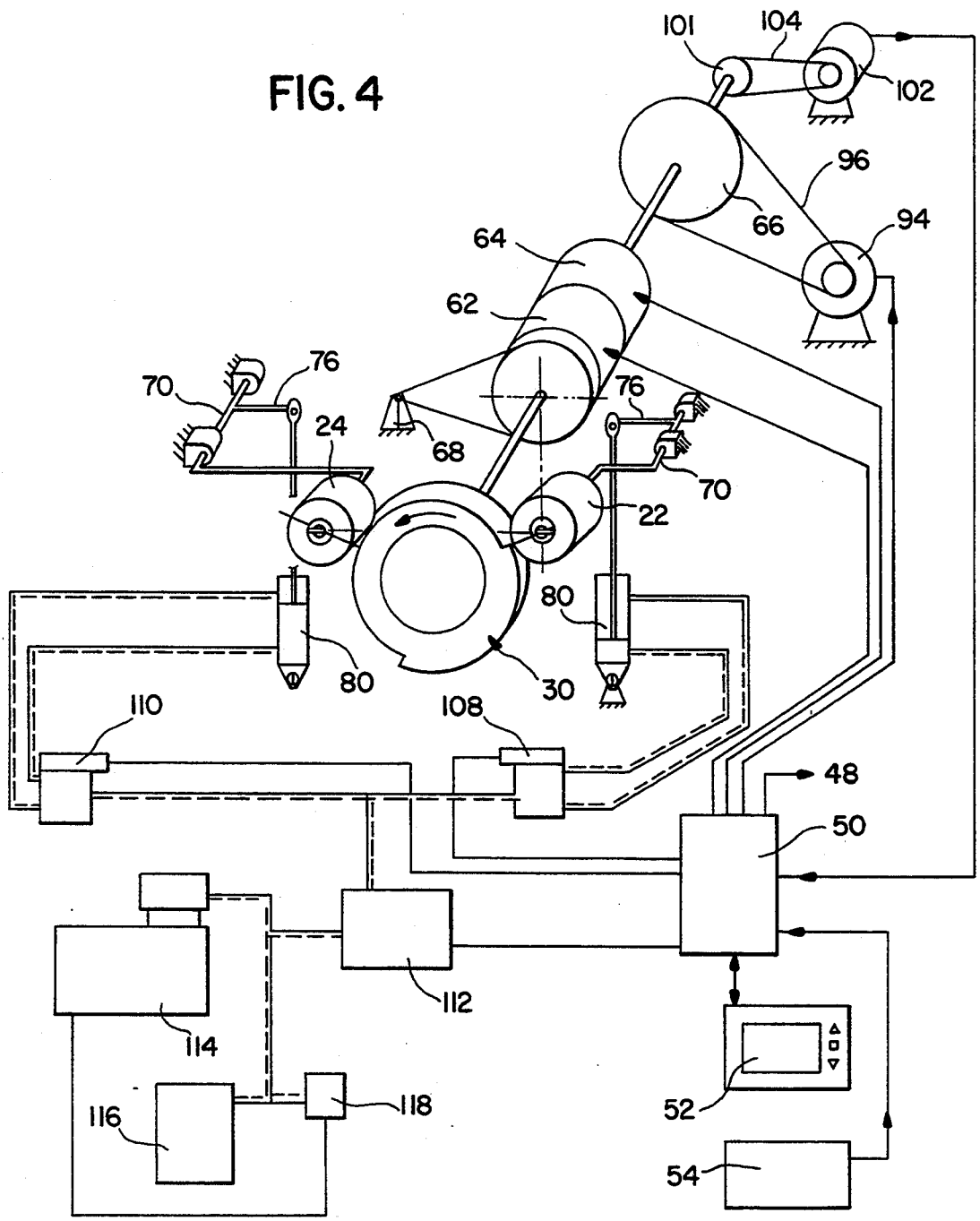
FIG. 4 is a schematic diagram of the testing system and apparatus of FIG. 2.

Referring to FIG. 4, there is shown a schematic diagram for the testing apparatus. FIG. 4 includes the mechanical drive system components for the sector 30 and the disks 22 and 24, as previously described, and the pneumatic and electrical system components of the preferred tester. A compressor 114 supplies, through air lines 84 and 86, compressed air to the pneumatic actuators 80. The compressed air is regulated by a pressure control 112 and directed by control valves 108 and 110. The pressure control 112 is accurate and repeatable to ±0.25% full scale.

The display 52 and the control panel 54 are used to program test data into the computer controller 50. The controller signals the pressure data to the pressure control 112 which maintains the desired pressure. The controller 50 also signals the control valves 108 and 110 to control the actuators 80 to engage or disengage the disks 22 or 24. The rotary encoder 102 continuously signals the position data for sector 30 to the controller 50. The controller 50 also controls the actuation of the brake 62 and the clutch 64, and controls the speed of the motor 94.

The operation of the testing apparatus 20 will be described with reference to FIGS. 1-5. A strip of test material is attached to the impression area 32 on the sector 30 by means of clamps (not shown) that are removably located in slots 31 on either end of the impression area 32. The sector 30 and the sector drive shaft 60 remain freely rotatable to facilitate installation of the test strip because the brake 62 is off and clutch 64 has not been engaged. The disks 22 and 24 are installed on respective spindles 72 on each disk positioning shaft 70.

Figure 5:
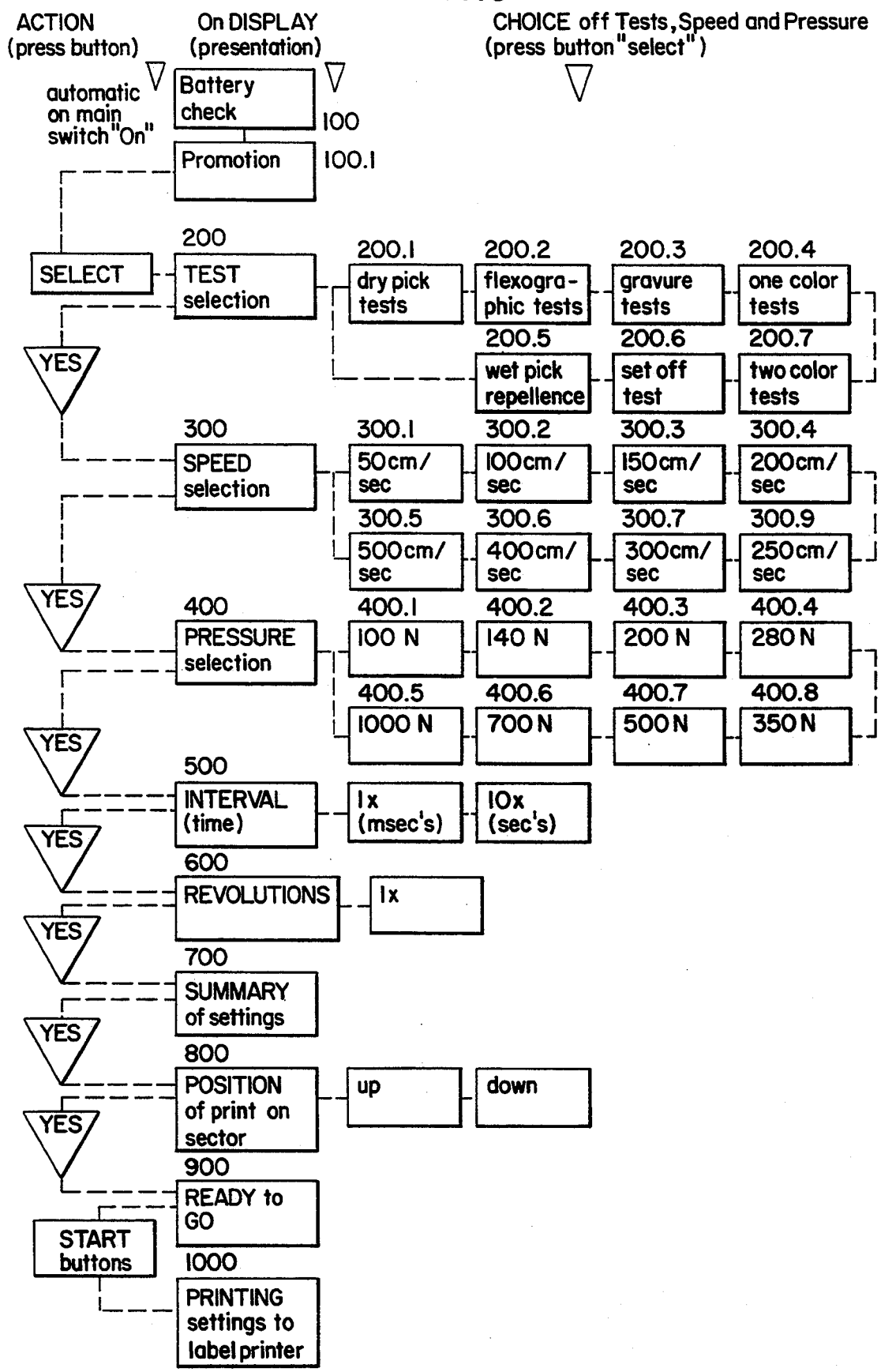
FIG. 5 is a flow diagram of the presently preferred programming options in the controller.

The controller 50 is programmed using the control panel 54 utilizing menu prompts which are presented on display 52. A flow diagram of the programming sequence is shown in FIG. 5. The operator is shown a variety of menu prompts on the display. Using these prompts, the operator programs the controller to perform the desired test. The desired speed, pressure, delay interval and number of revolutions are entered by the operator. A summary of the settings is then displayed before the test is started. If desired, a shift in the application point of the disk relative to the sector can then be set. On-line information screens describing each type of test are also available to the operator.

The speed of the motor 94 is signalled by the controller 50 to attain the desired speed selected by the operator. The clutch 64 is then engaged to couple the sector drive shaft 60 to the flywheel 66. As the sector 30 turns, the rotary encoder 102 transmits its position to the computer processor 50. When the sector 30 has been indexed such that the leading edge of the test strip on the impression area 32 is located under the first disk 22, the computer then signals the clutch 64 to disengage and the brake 62 to engage, stopping the sector 30 at the start position.

After the sector 30 has been indexed, the first control valve 108 is signaled by the controller 50 to trigger actuator 50 to bring the first disk 22 into contact with the sector 30. The actuator 80 pulls down on lever 76 causing the disk positioning shaft 70 to rotate counter-clockwise. As the shaft 70 rotates, the disk 22 is brought into contact with the sector 30. Compressed air from compressor 114 is regulated by pressure control 112 to the desired pressure. The pressure control 112 continuously monitors the pressure so it can be adjusted to create the required printing force during contact between the disk 22 and the sector 30. After contact, the clutch mechanism 64 is then signaled by the computer 50 to engage the sector drive shaft 60 to the spinning flywheel 66. The flywheel 66 has sufficient mass and stored energy to accelerate the sector 30 to the programmed speed. In the preferred embodiment, the sector 30 rotates in the counter-clockwise direction.

Friction between the sector 30 and the disk 22 causes the disk 22 to rotate against the test strip. After the desired portion of the test strip has been printed by the first disk 22, the computer 50 signals control valve 108 to reverse the actuator 80 and disengage the disk 22 from the sector 30.

If programmed for a delay interval, the sector drive shaft 60 is disengaged from the flywheel 66 and the sector is stopped by the brake 62 as the clutch mechanism 64 is disengaged by the controller 50. After the interval time has elapsed, the clutch is re-engaged by the controller 50. The second disk 24 is then brought into contact with the sector 30, in the same manner as the first disk 22, and the test is completed.

For certain tests, such as those requiring wetting or rewetting, the sector 30 can be rotated multiple revolutions, with disks 22 and/or 24 being brought into and out of contact with the test strip on the impression area 32 with each revolution. Delay intervals can also be set between each revolution. The relief portion 33 on the sector 30 insures that the disks do not inadvertently contact the sector during multiple revolution tests.

In other types of testing, the speed at which the sector rotates must be increased proportionally with the length of the print. For these types of tests, the operator can utilize the menu driven control panel 54 to program the starting velocity and the ending velocity for the print on a given test strip.

Upon completion of each test, the test strip is removed form the sector 30 and labeled with the test data for subsequent examination. If desired, the controller 50 can transmit the test settings from the testing apparatus to a label printer by means of a built-in connector (not shown) to print the labels. The connector can also be used by the manufacturer in conjunction with a regular telephone modem to provide long distance service for the tester. In the preferred embodiment, the connector is a RS-232 serial output connector. Alternatively, data on the test settings can be down-loaded to a computer or other storage media.

Before discussing additional embodiments, it will be useful to provide a discussion of the programming menus, an example of the programming procedure utilizing the menu prompts for a two color test will be described with reference to FIG. 5. When the testing apparatus 20 is first turned on it performs a battery check. The display 52 presents this data, shown as box 100, before automatically shifting to the next screen, shown as box 100.1 to display the promotional information. The operator is then prompted by the test selection menu, shown as box 200, to select one of the various tests shown in boxes 200.1 through 200.7. For this example, box 200.7 is selected and the operator confirms the selection by pressing the "YES" key.

The controller then prompts the operator to select the variables required for a specific test. The next menu, shown as box 300, is the speed selection menu. The operator selects the desired speed for the test from the available choices shown in boxes 300.1 through 300.6. For this example a speed of 50 cm/sec, shown in box 300.1 is selected. The next menu, shown as box 400, prompts the operator to select the desired pressure with which the disks will be applied to the sector 30. The various choices for application pressures are shown in boxes 400.1 through 400.8. For this example, a pressure of 100 N, shown in box 400.1, is selected. The next menu, shown as box 500, prompts the operator to input a delay time. Delay intervals of up to 9.9 seconds, in various combinations of seconds and milliseconds, can be input by the operator through the control panel 54. For this example a delay interval of 1 second is input. The next menu, shown as box 600, prompts the operator to input the desired number of revolutions. The input for the number of revolutions is made through the control panel 54. For this example, a single revolution is input. The next menu, shown as box 700, then displays a summary of all the previous test settings. The next menu, shown as box 800, then prompts the operator to indicate if a shift in the start position for the test strip is desired. For this example, no shift is desired. The next menu, shown as box 900, indicates that the apparatus is ready to start. Once the settings have been completed, the operator must engage both start buttons 65 in order to begin the test. An additional menu, shown as box 1000, prompts the operator to download the test data to a printer.

Figure 6:
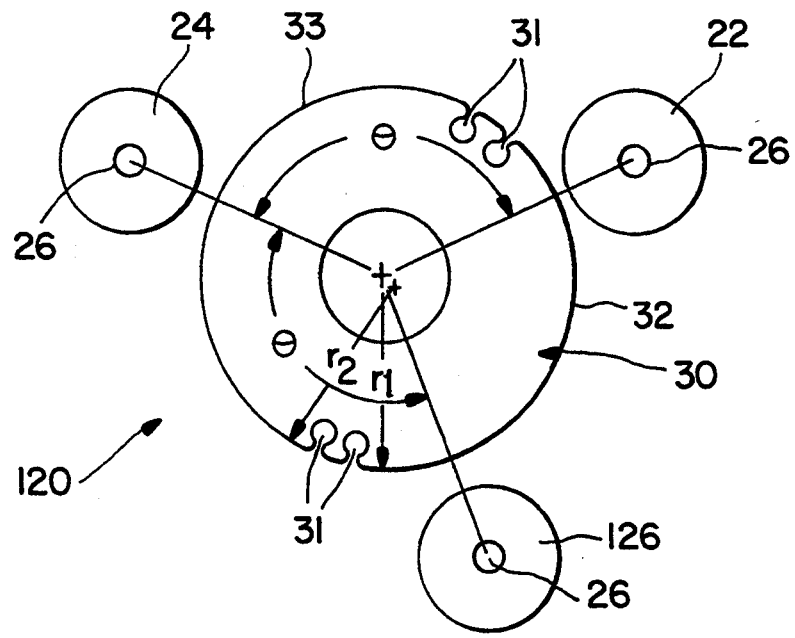
FIG. 6 is a front view similar to FIG. 2 of a second embodiment of the invention.

Referring now to FIG. 6, a second embodiment of the invention 120 is shown. A third independently movable disk 126, located adjacent to the sector 30, has been added to the testing apparatus. The disk 126 can be used in tests to apply printing ink or other test coatings against the test strip mounted on the sector 30 in conjunction with the first two disks 22 and 24. The third disk 126 is located at a distance Θ° in the counter-clockwise direction of rotation of the sector 30 from the second disk 24. In this second embodiment, Θ is approximately 135° or greater. By utilizing the same geometry as previously described in the first embodiment in conjunction with the ability to program multiple revolutions, it is possible to make single, double or triple prints utilizing up to three colors printed partially or fully on top of each other. With each disk 22, 24 and 126 being independently movable into and out of contact with the sector 31 and utilizing various delay intervals and different speeds, it is possible to carry out a variety of tests utilizing multiple impressions on a single test strip.

The mechanical drive system configuration and controls for movement of the third disk 126 into and out of contact with the sector is similar to the system previously described in conjunction with the first embodiment. The disk 126 utilizes a third disk positioning shaft 70. This is installed in the housing 36 in a similar fashion to the disk positioning shafts 70 previously described. A third pneumatic cylinder 80, controlled by the computer 50, would be provided to move the third disk 126 into and out of contact with the sector 30 at the programmed time and position.

Figure 7:
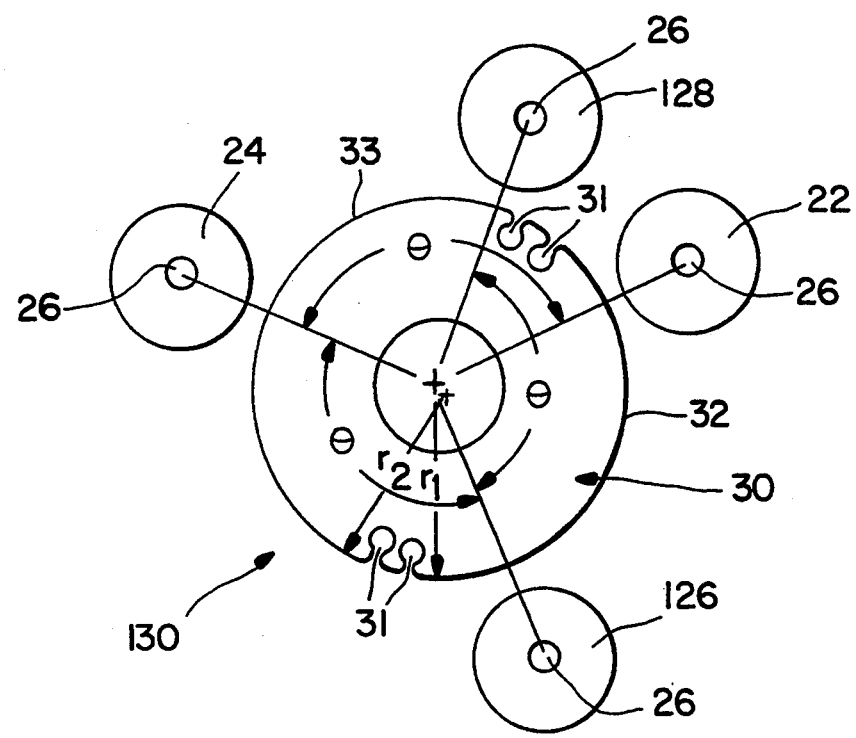
FIG. 7 is a front view similar to FIG. 6 of a third embodiment of the invention.

A third embodiment of the testing apparatus 130 is shown in FIG. 7. The third embodiment is similar to the second embodiment except a fourth disk 128 has been added. The fourth disk 132 is at a distance Θ° in the counter-clockwise direction of rotation of the sector 30 from the third disk 126. The fourth disk 132 is also independently controlled for movement into and out of contact with the sector 30 in a similar fashion to the second embodiment of the invention. The computer controller 50 can be programmed to independently move each of the four disks into and out of contact with the test strip mounted on the sector 30 at the speeds, pressures, intervals, revolutions and offsets desired. By utilizing four disks in conjunction with the ability of the sector to make multiple revolutions, the four different inks or coating materials may be tested on the same strip. If desired, different materials may be tested on different disks during a single test run.

It will be recognized by those skilled in the art that the testing apparatus of the present invention provides increased flexibility for the testing of printing materials. It will also be appreciated that the testing apparatus can have a variety of forms without departing from the scope of the present invention.

We claim:

1. A testing apparatus for examining printing materials, the apparatus comprising:
   a rotatable sector that is capable of multiple rotations for a single test strip at selected, controlled speeds including means for continuously determining the sector's rotary position;
   a drive means for rotating the sector;
   at least two rotatable disks mounted adjacent to the sector for movement into and out of contact with the sector;
   disk control means for independently moving the rotatable disks into and out of contact with the sector at any desired sector position with each revolution of the sector and for controlling the pressure with which each disk is applied between the sector and the rotatable disk when an impression is produced; and
   a programmable controller which communicates with the sector drive means and the disk control means and controls the speed and position of the sector and the movement and contact pressure of the disks relative to the sector.

2. The apparatus of claim 1 wherein the disk control means is pneumatic.

3. The apparatus of claim 1 wherein there are two rotatable disks and they are spaced apart by an angle of approximately 135°.

4. The apparatus of claim 1 wherein there are three rotatable disks, each of the disks being spaced from the previous disk by approximately 135° taken in the direction of rotation of the sector.

5. The apparatus of claim 1 wherein there are four rotatable disks, each of the disks being spaced from the previous disk by approximately 135° taken in the direction of rotation of the sector.

6. The apparatus of claim 1 wherein the spacing of the disks taken in the direction of rotation of the sector is equal to or greater than the arc length of a test strip mounted on the sector.

7. The apparatus of claim 1 further comprising a means for transmitting the controller data to a label printer.

8. The apparatus of claim 1 wherein the controller data is transmitted to a computer for storage.

9. A testing apparatus for examining printing materials, the apparatus comprising:
   a rotatable sector that is capable of multiple rotations for a single test strip at selected, controlled speeds and accelerations;
   location means for continuously determining the sector's rotary position;
   a flywheel to store energy required to rapidly accelerate the sector;
   an electric motor for rotating and accelerating the sector and the flywheel;
   a clutch mechanism between the sector to the flywheel;
   two rotatable disks mounted adjacent to the sector for movement into and out of contact with the sector at any desired sector position;
   positioning means for moving the rotatable disks and for outputting data with respect to the pressure with which the disks are applied to the sector; and
   a programmable controller which communicates with the motor, the location means and the positioning means and controls the speed and position of the sector and the movement and contact pressure of the disks relative to the sector.

10. An apparatus for testing printing materials, the apparatus comprising:
   a rotatable, material holding sector capable of multiple rotations for a single test strip;
   drive means for rotating the sector at selected, controlled speeds;
   generating means for outputting data on the sector's rotary position;
   at least one rotatable disk mounted adjacent to the sector for movement into and out of contact with the material holding portion of the sector at any desired sector position;
   fluid drive means for independently moving the rotatable disk into and out of contact with the sector and for outputting data with respect to the pressure with which the disk is applied to the sector; and
   a controller which communicates with the drive means, the generating means and the fluid drive means and controls the speed and position of the sector and the movement and contact pressure of the disk relative to the sector.

11. The apparatus of claim 10 wherein the fluid drive means is pneumatic.

12. The apparatus of claim 10 wherein there are two rotatable disks and they are spaced apart by an angle of approximately 135°.

13. The apparatus of claim 10 wherein there are two rotatable disks and the spacing between the disks in the direction of rotation of the sector defines an arc length that is at least equal to the length of a test strip mounted on the sector.

14. The apparatus of claim 10 wherein there are three rotatable disks, each of the disks being spaced from the previous disk in the direction of rotation of the sector by an angle of approximately 135°.

15. The apparatus of claim 10 wherein there are three rotatable disks and the spacing between the disks in the direction of rotation of the sector defines an arc length that is at least equal to the length of a test strip mounted on the sector.

16. The apparatus of claim 10 wherein there are four rotatable disks, each of the disks being spaced from the previous disk in the direction of rotation of the sector by an angle of approximately 135°.

17. The apparatus of claim 10 wherein there are four rotatable disks and the spacing between the disks in the direction of rotation of the sector defines an arc that is at least equal to the length of a test strip mounted on the sector.

18. The apparatus of claim 16 wherein each disk is associated with a separate, respective fluid drive means.

19. The apparatus of claim 10 further comprising a means for transmitting data from the controller to a label printer.

20. The apparatus of claim 10 further comprising a means for transmitting data from the controller to a data storage device.

* * * * *

UNITED STATES PATENT AND TRADEMARK OFFICE
CERTIFICATE OF CORRECTION

PATENT NO. : 5,415,054
DATED : May 16, 1995
INVENTOR(S) : Ferdinand A. De Vos, Sr., et al It is certified that error appears in the above-indentified patent and that said Letters Patent is hereby corrected as shown below:

On the title page:

At [75] Inventors, please insert --Ferdinand A. de Vos, Jr., Netherlands--.

Signed and Sealed this

Twenty-eighth Day of November 1995

Attest:

BRUCE LEHMAN

*Attesting Officer*    *Commissioner of Patents and Trademarks*